United States Patent [19]
Christensen et al.

[11] Patent Number: 6,156,548
[45] Date of Patent: Dec. 5, 2000

[54] IMMOBILIZATION OF ENZYMES WITH A FLUIDIZED BED FOR USE IN AN ORGANIC MEDIUM

[75] Inventors: Morten Würtz Christensen, Lyngby; Ole Kirk, Virum; Christian Pedersen, Roedovre, all of Denmark

[73] Assignee: Novo Nordisk A/S, Bagsvaerd, Denmark

[21] Appl. No.: 09/210,192

[22] Filed: Dec. 11, 1998

Related U.S. Application Data

[60] Provisional application No. 60/074,189, Feb. 10, 1998.

[30] Foreign Application Priority Data

Dec. 23, 1997 [DK] Denmark ................... 1527/97

[51] Int. Cl.$^7$ .............. C12P 7/64; C12N 11/14; C12N 11/08
[52] U.S. Cl. ............ 435/134; 435/176; 435/180
[58] Field of Search .................. 435/174, 176, 435/180, 134

[56] References Cited

U.S. PATENT DOCUMENTS

| | | | |
|---|---|---|---|
| 4,689,297 | 8/1987 | Good et al. ............ | 435/174 |
| 5,814,501 | 9/1998 | Becker et al. .......... | 435/174 |
| 5,879,920 | 3/1999 | Dale et al. ............. | 435/187 |

FOREIGN PATENT DOCUMENTS

| | | |
|---|---|---|
| 0 140 542 | 5/1985 | European Pat. Off. . |
| WO 94/26883 | 11/1994 | WIPO . |
| WO 95/22606 | 8/1995 | WIPO . |

*Primary Examiner*—David M. Naff
*Attorney, Agent, or Firm*—Elias J. Lambiris; Carol E. Rozek

[57] ABSTRACT

An immobilized enzyme preparation for use in an organic medium essentially devoid of free water is prepared using a fluidized bed. An enzyme-containing liquid medium is contacted with a particulate porous carrier which preferably has a particle size of 200–1000 μm and a surface area of 20–1000 m$^2$/g, and volatile components of the liquid medium are removed to fix or adsorb the enzyme on the carrier. The carrier may have a hydrophilic surface and an amount of liquid medium is used to prevent agglomeration of the carrier. The enzyme can be adsorbed on a carrier having a hydrophobic surface, and the addition of a hygroscopic substance suppresses agglomeration of the carrier by absorbing excess liquid. The hygroscopic substance may be removed during the removal of volatile components. Contacting of the enzyme-containing liquid and carrier is in a fluidized bed where immobilization and removing volatile components are conducted simultaneously, or contacting is in mixer followed by removing volatile components in a fluidized bed. The enzyme-containing liquid may be atomized onto the carrier in the fluidized bed or in the mixer. Enzymes immobilized include lipase, and the immobilized lipase is used in a trans-esterification reaction.

27 Claims, 1 Drawing Sheet

Fig. 1: Acidolysis
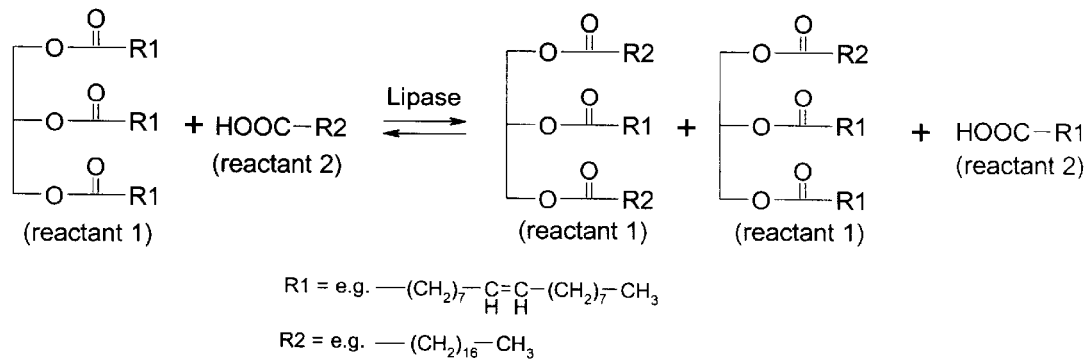
Fig. 2: Inter-esterification
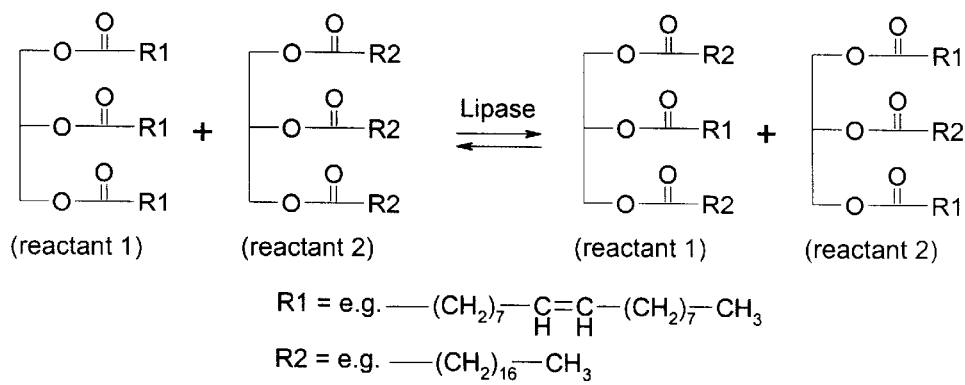
Fig. 3: Alcoholysis
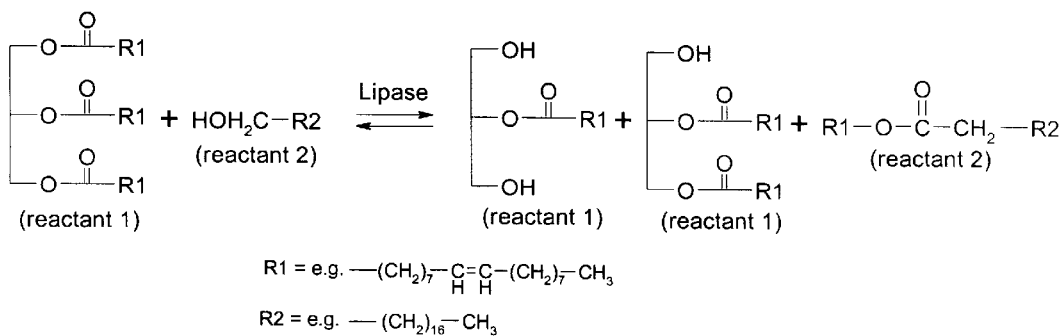

IMMOBILIZATION OF ENZYMES WITH A FLUIDIZED BED FOR USE IN AN ORGANIC MEDIUM

CROSS-REFERENCE TO RELATED APPLICATIONS

This application claims priority under 35 U.S.C. 119 of U.S. provisional application Ser. No. 60/074,189 filed Feb. 10, 1998 and Danish application 1527/97 filed Dec. 23, 1997, the contents of which are fully incorporated herein by reference.

FIELD OF THE INVENTION

The invention relates to a process for producing an immobilized enzyme preparation for use in a mainly organic medium essentially devoid of free water, and use of the immobilized enzyme preparation for organic synthesis.

BACKGROUND OF THE INVENTION

Immobilized enzymes are known to be used for organic synthesis.

The most commonly immobilized enzymes are lipases used for esterification reactions in mainly organic media essentially devoid of free water.

EP 140542 B2 describes a process, wherein an enzyme containing liquid is brought in contact with a weak anion exchange resin carrier by dispersing the carrier in the liquid and mixing by stirring with a magnetic stirrer, whereby the enzyme is immobilized on the carrier. The immobilization is subsequently followed by vacuum drying of the enzyme-carrier.

WO 95/22606 describes a process, wherein an enzyme containing liquid is brought in contact with a porous silica carrier by atomizing the liquid onto the carrier in a mixer, subsequently followed by drying overnight at ambient conditions.

In industrial immobilization processes described in prior art, the carrier or support material is placed in a column shaped adsorption vessel and an enzyme containing liquid is recirculated until sufficient adsorption of the enzyme on the carrier has been obtained. Following the adsorption step the column is emptied by manually shoveling the enzyme-carrier product into trays. The product is then dried by placing the trays under vacuum at room temperature for a period of 14–16 hours.

Wo 94/26883 describes a process for producing dust-free enzyme granules by absorbing the enzyme on a porous material, said material including NaCl, Soda, and silica, and optionally coating the product with a protective outer layer. Generally immobilization of enzymes should not be compared with granulation of enzymes as granulation serves a completely different purpose, viz. to provide a preferably non-dusting delivery material from which an enzyme may be delivered to an aqueous solution by disintegration of the granule and/or dissolution of the enzyme in the aqueous phase. Enzyme immobilization concerns immobilizing an enzyme product on a carrier on which the enzyme is fixed and yet functional and for which the enzyme is not liberated to the solvent to which it is applied.

Immobilization processes known to the art are limited in capacity as they involve laborious and manual steps and require heavy equipment investments (e.g. vacuum rooms), which, in turn, means inflexible production and expensive products.

SUMMARY OF THE INVENTION

The present invention provides alternative processes for industrial immobilization of enzymes, which significantly increases capacity and reduces labor costs, by means of standard multi-purpose process equipment.

Thus the invention provides processes for producing an immobilized enzyme preparation for use in a mainly organic medium essentially devoid of free water, which in a first aspect comprises:
a) fluidizing a particulate porous carrier in a fluid bed,
b) introducing an enzyme containing liquid medium by atomization into the fluid bed, so as to adsorb the enzyme on the carrier, and
c) removing volatile components of the liquid medium from the carrier in the fluidized bed.

In a second aspect the process comprises:
a) contacting an enzyme containing liquid medium with a particulate porous carrier having a substantially hydrophobic surface, so as to adsorb the enzyme on the carrier,
b) introducing a particulate hygroscopic substance, so as to suppress agglomeration of the carrier, and
c) removing volatile components of the liquid medium and the hygroscopic substance from the resulting product in a fluidized bed.

Finally in a third aspect the process comprises:
a) introducing an enzyme containing liquid medium by atomization onto a particulate porous carrier having a substantially hydrophilic surface, so as to adsorb the enzyme on the carrier, wherein the liquid is introduced in an amount such that substantially no agglomeration of the carrier occurs and
b) removing volatile components of the liquid medium from the resulting product in a fluidized bed.

BRIEF DESCRIPTION OF THE DRAWINGS

FIGS. 1, 2 and 3 show a transesterification process using an immobilized lipase produced according to the present invention.

DETAILED DESCRIPTION OF THE INVENTION

The Carrier

In the embodiment of the invention the carrier is a particulate porous material. The particles may suitably be of a diametrical size of 200–1000 $\mu$m, preferably 400–700 $\mu$m; have a surface area of 20–1000 $m^2/g$, preferably 100–700 $m^2/g$ and have a pore size of 10–500 nm, preferably 100–300 nm.

The carrier particles may comprise inorganic, organic or both inorganic and organic material. Said carrier may further have a hydrophilic or hydrophobic surface.

In a first embodiment of the invention the carrier particles comprise an inorganic material with a substantially hydrophilic surface, which is essentially insoluble in hydrophilic or hydrophobic liquids or mixtures thereof. Preferred carriers may be based on silicas (e.g. Celite from Manville, USA), zeolites (e.g. Wessalith MS330 from Degussa, Germany), aluminas, ceramics (e.g. as disclosed in Yoshihiko Hirose et Al. (Proceedings from 3$^{rd}$ International Symposium on Biocatalysis and Biotransformations, La Grande Motte, France, 1997, p238) and kaolins (e.g. kaolin's subjected to acid, hydrothermal and baking treatment as disclosed in U.S. Pat. No. 5,614,401).

In a second embodiment of the invention the carrier particles comprise a hydrophilic inorganic material as described in the first embodiment coated with organic moieties thus having a substantially hydrophobic surface, e.g. as described in JP 09000257-A, wherein an acid treated kaolin carrier is coated with N-phenyl-gamma-aminopropyltrimethoxysilane. Further carriers are described in JP 08126489-A, wherein a water insoluble carrier is coated with a polymer forming a disulphide linkage with enzymes. A third type of carrier is described in *Biotechnology Techniques* vol. 3 No 5 345–348, wherein a ceramic carrier is coated with polyethylene amine, polyethylene imine or 3-aminopropyltriethoxysilane, all three surface types allowing an enzyme to be covalently bound via glutaraldehyde coupling.

In a third embodiment of the invention the carrier particles comprise an organic polymer resin with a substantially hydrophobic surface. The resin may be an adsorbent resin, preferably a polyacrylate, a polymethacrylate (e.g. polymethyl methacrylate), polystyrene cross-linked with divinylbenzene, polyurethane or polypropylene or the resin may be an ion exchange resin, preferably an anion exchange resin, e.g. a weakly basic anion exchange resin. A preferred anion exchange resin is a phenolic type Duolite resin from Rohm & Haas.

Further the carrier may be made from regenerated chitosan as disclosed in DE 4429018-A.

The Enzyme

The enzyme to be immobilized according to the invention may be any enzyme suitable for use in media essentially devoid of free water. The most commonly used enzymes are lipases and in a specific embodiment of the invention the lipase may be derived from a strain of the genus Humicola (also known as Thermomyces), Pseudomonas, Candida, or Rhizomucor, preferably the species *H. lanuginosa* (also known as *Thermomyces lanuginosa* as described in U.S. Pat. No. 4,810,414 and EP 305216 which are hereby included by reference), *C. antarctica* or *R. miehei*.

Further the lipase may be positionally site specific (i.e. 1,3 specific) or non-specific, upon interaction with triglycerides as substrates.

The enzyme may further be covalently cross-linked by glutaraldehyde treatment during the immobilization process.

The enzyme containing liquid medium

The enzyme containing liquid medium is a hydrophilic medium, preferably aqueous. It may thus contain more than 20% water, preferably more than 40% water, more preferably more than 50% water, more preferably more than 60% water, more preferably more than 70% water, more preferably more than 80% water, more preferably more than 90% water, e.g. more than 95% water. It may contain other organic or biological matter. Thus it may be a fermentation broth or an enzyme concentrate solution obtainable by purifying a fermentation broth by e.g. ultra filtration or by protein precipitation, separation and re-dissolution in an other aqueous medium. It may further be substantially pure enzyme dissolved in an aqueous medium. In a special embodiment of the invention the enzyme containing aqueous liquid has not been subjected to costly processing steps prior to immobilization to remove water such as evaporation nor has it been subjected to addition of non aqueous solvents, e.g. organic solvents such as alcohols, e.g. (poly) ethylene glycol and/or (poly) propylene glycol.

The immobilization process

Immobilization of enzyme on carriers with a hydrophilic surface

Without being bound to the theory it is contemplated that immobilization of enzyme on carriers having a substantially hydrophilic surface involves no adsorption of the enzyme, but is a deposition of enzyme in surface pores as a result of removal of the liquid, in which the enzyme is dissolved.

i. In one embodiment of the invention the immobilization of enzyme on a carrier having a substantially hydrophilic surface may thus be conducted in standard mixing equipment (e.g. Lodiger, Germany), wherein an enzyme containing liquid is introduced by atomization to the dry porous and particulate carrier during mixing, e.g. using a nebulizer connected to a pump (e.g. a standard peristaltic Watson-Marlow pump).

The liquid should be added in such amounts that substantially no agglomeration of the carrier occurs, thus enabling the subsequent drying of the enzyme-carrier product by fluidizing said product in standard fluid bed equipment, e.g. a Uni-Glatt fluidized bed apparatus (Glatt, Germany), thereby removing volatile components.

ii. In a second embodiment of the invention the immobilization of enzyme on a carrier having a substantially hydrophilic surface may alternatively be conducted in standard fluid bed equipment, e.g. a Uni-Glatt fluidized bed apparatus (Glatt, Germany), wherein the dry porous and particulate carrier is fluidized and an enzyme containing liquid at ambient temperature is introduced by atomization to the fluidized carrier, e.g. using a nebulizer connected to a pump (e.g. a standard peristaltic Watson-Marlow pump). In this embodiment immobilization and drying are conducted simultaneously.

Immobilization on carriers with a hydrophobic surface

Without being bound to the theory it is contemplated that immobilization of enzyme on carriers having a substantially hydrophobic surface involves adsorption of the enzyme on the surface. The immobilization may be enabled by the enzyme forming hydrogen bonds, ionic bonds or covalent bonds with moieties in the surface.

iii. In a third embodiment of the invention the immobilization of enzyme on a carrier having a substantially hydrophobic surface may thus be conducted in standard mixing equipment, wherein an enzyme containing liquid is introduced to the dry porous and particulate carrier in an amount sufficient to form a paste or a slurry. The paste or slurry is mixed for a period of time in which the enzyme is adsorbed. Following the adsorption step a hygroscopic particulate substance of a particle size smaller than the carrier is introduced to the slurry or paste. Said substance substantially prevents agglomeration of the enzyme-carrier by adsorption of excess liquid, thereby enabling the subsequent drying of the enzyme-carrier product by fluidizing said product in standard fluid bed equipment, e.g. a Uni-Glatt fluidized bed apparatus (Glatt, Germany), thereby removing volatile components and if necessary the hygroscopic substance. The hygroscopic substance may be any particulate fine ground hydrophilic components capable of absorbing excess liquid such as silicas (e.g. Hyper Flow Celite), kaolin, aluminas, zeolites or ceramics. Removal of the hygroscopic substance may be achieved by inserting a filter at the top of the fluidized bed with a suitable pore size which will allow the hygroscopic substance to pass but will retain the enzyme-carrier. A pore size of 100–900 $\mu$m, preferably 200–400 $\mu$m may be employed.

iv. In a fourth embodiment of the invention the immobilization of enzyme on a carrier having a substantially hydrophobic surface may alternatively be conducted in standard fluid bed equipment, e.g. a Uni-Glatt fluidized bed apparatus (Glatt, Germany), wherein the dry porous and particulate carrier is fluidized and an enzyme containing liquid at ambient temperature is introduced by atomization to the fluidized carrier, e.g. using a nebulizer connected to a pump (e.g. a standard peristaltic Watson-Marlow pump). In this embodiment immobilization and drying are conducted simultaneously.

Common features for i and iii mixing step

Immobilizing the enzyme on the carrier in a mixer may suitably be conducted at ambient temperature. Mixing times may for this size of equipment suitably be 5–60 minutes, preferably 10–30 minutes.

Common features for i, ii, iii and iv fluid bed step

A suitable air inlet flow in the fluid bed equipment will depend on the size and density of the enzyme-carrier, the amount of carrier and the fluid bed equipment. Further the air inlet flow has an upper limit, as the flow should be sufficient to keep the enzyme-carrier fluidized, but not so powerful as to "blow off" the enzyme-carrier.

Suitable temperatures of the inlet air for removing volatile components will primarily depend of the thermal stability of the enzyme (the inactivation temperature). The temperature may be 40–90° C., preferably 50–70° C., e.g. 60° C. A higher temperature provides shorter immobilization and drying times.

Further, time consumption for immobilization and/or drying of the enzyme-carrier when equipment, air inlet flow and air temperature are fixed will depend on the quantity of enzyme-carrier. The immobilization/drying process may be monitored by measuring the air inlet temperature and the air outlet temperature. While the enzyme-carrier is moist the outlet temperature is lower than the inlet temperature due to the heat absorption and evaporation of volatile components. Typically a steady state evaporation occurs during the immobilization/drying process where the outlet temperature stabilizes on a temperature lower than the inlet temperature indicating that evaporation of volatile components (i.e. heat absorption) occurs at a constant rate. At the end of the immobilization/drying process the outlet temperature begins to rise and approach the inlet temperature indicating that the heat absorption has decreased and thus the moisture of the enzyme-carrier has been removed. Using a fluid bed for immobilization and drying simultaneously the drying process will occur for as long as the enzyme containing liquid is atomized into the fluid bed, and may suitably be extended for 5–30 minutes after inlet of the enzyme containing liquid has ended.

An important aspect of the invention is that the immobilization processes can be easily scaled up by applying other larger standard equipment. Thus the equipment setting ranges given vide supra may be adjusted to optimize larger scale equipment.

Uses of immobilized enzyme preparation

Immobilized enzyme prepared in context of the invention may be used for hydrolysis, synthesis or modification of organic substances in a medium essentially devoid of free water. Said substances may be comprised in food products like plant or animal oils/fats.

Accordingly the invention encompasses a process for enzymatic modification of an organic compound comprising contacting in a reaction medium essentially devoid of free water said organic compound with an immobilized enzyme produced according to the invention.

In a preferred embodiment of the invention an immobilized lipase enzyme, e.g. a 1,3 specific lipase, is used for an transesterification process in a medium essentially devoid of free water. The trans-esterification may be used for fatty acid substitution, comprising contacting a first reactant and a second reactant with said immobilized lipase by which a substitution reaction occurs, e.g. as shown in FIGS. 1–3.

The first reactant may be a fatty acid ester, preferably a triglyceride or a mixture of triglycerides.

The second reactant may be another fatty acid ester different from the first reactant, preferably a triglyceride or a mixture of triglycerides. Further the second reactant may be an alcohol or a free fatty acid.

The medium in this preferred embodiment of the invention comprises an organic solvent, or it may consist essentially of triglycerides.

Said use of the invention may be applied in production of food products e.g. margarine or cocoa-butter substitutes.

The invention is illustrated by the following non-limiting examples.

EXAMPLES

Lipase assay:

The lipolytic activity may be determined using tributyrine as substrate. This method is based on the hydrolysis of tributyrine by the enzyme, and the alkali consumption is registered as a function of time.

One Lipase Unit (LU) is defined as the amount of enzyme which, under standard conditions (i.e. at 30.0° C.; pH 7.0; with Gum Arabic as emulsifier and tributyrine as substrate) liberates 1 mmole titrable butyric acid per minute.

A folder AF 95/5 describing this analytical method in more detail is available upon request to Novo Nordisk A/S, Denmark.

Trans-esterification assay a) 200 mg Trilaurin (Fluka) and 571 mg of myristic acid (8 molar equivalents) of myristic acid (Merck) was dissolved in 20 ml heptane. 3 ml saturated NaCl solution was added and the mixture was stirred in a closed bottle for 24 hours at ambient temperature.

b) The immobilized enzyme (50 mg) was water equilibrated in a dissicator (hermetically closed vessel) for 24 hours, using gas phase equilibrium with a saturated NaCl solution (water activity=0.75).

c) At T=0 minutes the water equilibrated immobilized enzyme and substrate were mixed in a closed bottle, which was placed in a shaking bath at 40° C. 100 µl samples were withdrawn from the closed bottle using a syringe at T=0, 10, 20, 30, 40, 50 and 60 minutes. The samples were diluted (1:5 vol:vol) with a 50/50 (% v/v) mixture of acetone/acetonitrile and analyzed on an HPLC system.

Analysis on the HPLC system:

d) The HPLC system was equipped with a LiChrosphere 100 RPC18 endcapped 5 µm (125×4 mm) column (Merck). A 50/50 (% v/v) isocratic acetonitrile/acetone solution was selected as the mobile phase with a flow of 1 ml/minute.

e) 20 µl of sample was injected and the formed products (1,2-dilauroyl-3-myristoyl-glycerol (product 1) and 1,3-dimyristoyl-2-lauroyl-glycerol (product 2)) were measured by evaporative light scattering detection (Sedex 55, Sedere, France) at 2 bar pressure and a temperature at 30° C.

f) The amounts of formed products were estimated by comparing sample measurements to external standard curves of 1,2-dilauroyl-3-myristoyl-glycerol and 1,3-dimyristoyl-2-lauroyl-glycerol.

The rate of the trans-esterification process may be calculated in units, where 1 unit is defined as 1 µmole myristic acid incorporated in trilaurin per minute.

Alternatively the effect of the inter-esterification process may be stated in % conversion of trilaurin to product 1 and product 2, which is calculated by:

$$\% \ Conversion_{T=i} = \left[ \frac{mole \ product \ 1 + mole \ product \ 2}{mole \ trilaurin \ at \ T = 0} \right]_{T=i} \cdot 100\%$$

where i indicates at which time the sample is withdrawn from the incubation bottle (step c).

Example 1

Lipase adsorption onto zeolite based carrier in fluid bed with simultaneous removal/evaporation of volatile liquids 400 g of a solution of *Humicola lanuginosa* lipase (693 kLU/ml) was atomized onto 1 kg zeolite (Wessalith MS330; 0.5–0.9 mm; Degussa, Germany) using a two-way nebulizer in a Uni-Glatt (Glatt, Germany) fluidized bed apparatus. The lipase solution was applied via a peristaltic pump (Watson-Marlow). Inlet air temperature was 60° C. and product temperature was 40° C. with an air flow at 100 m3/hours. After the immobilization was finished the product was dried for an additional 5 minutes in the fluid bed.

The immobilization process was tested on the inter-esterification assay, which measured 53% conversion of trilaurin after T=24 hours

Example 2

Lipase adsorption onto silica based carrier in fluid bed with simultaneous removal/evaporation of volatile liquids.

94 g of a solution of *Humicola lanuginosa* lipase (693 kLU/ml) fermentation solution was diluted with 100 g of demineralized water and atomized onto 200 g of Celite R648 (Manville, USA) in a Uni-Glatt (Glatt, Germany) fluidized bed apparatus, using a two-way nebulizer (made in-house). The lipase solution was applied via a peristaltic pump (Watson-Marlow)(flow rate 238 g/hour). Inlet air temperature and product temperature were identical with those indicated in example 1. After the immobilization was finished the product was dried for an additional 5 minutes in the fluid bed.

The immobilization process was tested on the inter-esterification assay, which measured 12% conversion of trilaurin after T=24 hours

Example 3

Lipase adsorption onto adsorbent resin in mixer and subsequent drying in fluid bed using Hyper Flow Celite (HFC) as drying aid.

94 g of a solution of *Humicola lanuginosa* lipase (693 kLU/ml) was diluted with 260 g demineralized water. The solution was added to 250 g adsorbent resin (a macro-porous divinylbenzene cross-linked polystyrene, Purolite AP 1090; from Purolite, UK) in a 5 l mixer (Lodiger, Germany). The suspension was mixed for 20 minutes at ambient temperature and with RPM of 30. 200 g Hyper Flow Celite (HFC) was added to absorb residual liquid enabling the mixture to be fluidized in the Uni-Glatt apparatus. Using the same conditions as described in example 1, the mixture was dried for 20 minutes. In this period, the HFC was separated from the adsorbent resin using a 300 μm filter on the top of the fluid bed to retain the resin particles while HFC was blown off.

Activity of product:
The rate for T=0–60 minutes was measured to 3.9 U/g product.

Example 4

Lipase adsorption onto adsorbent resin in fluid bed with simultaneous drying of volatile liquids.

94 g of a solution of *Humicola lanuginosa* lipase (693 kLU/ml) was diluted with 200 g of demineralized water and atomized onto 200 g of adsorbent resin (macro-porous divinylbenzene cross-linked polystyrene, Purolite AP 1090; from Purolite, UK) in a Uni-Glatt (Glatt, Germany) fluidized bed apparatus, using a two-way nebulizer. The lipase solution was applied via a peristaltic pump (Watson-Marlow) (flow rate 238 g/hour). Inlet air temperature and product temperature were 50° C. and 30° C., respectively. After the immobilization was finished the product was dried for an additional 5 minutes in the fluid bed (flow rate 100 m3/hour).

The immobilization process was tested on the inter-esterification assay, which measured 36% conversion of trilaurin after T=24 hours.

Example 5

Lipase adsorption onto a kaolin based carrier in fluid bed with simultaneous drying of volatile liquids.

94 g of a solution of *Humicola lanuginosa* lipase (693 kLU/ml) was diluted with 300 g of demineralized water and atomized onto 200 g of kaolin carrier (BIOFIX SC (500–250); from ECC, UK) in a Uni-Glatt (Glatt, Germany) fluidized bed apparatus, using a two-way nebulizer (made in-house). The lipase solution was applied via a peristaltic pump (Watson-Marlow)(flow rate 238 g/hour). Inlet air temperature and product temperature were 50° C. and 30° C., respectively. After the immobilization was finished the product was dried for an additional 5 minutes in the fluid bed (flow rate 100 m3/hour).

The immobilization process was tested on the inter-esterification assay, which measured 34% conversion of trilaurin after T=24 hours.

What is claimed is:

1. A process for producing an immobilized enzyme preparation for use in an organic medium essentially devoid of free water, comprising:
   a) fluidizing a particulate porous carrier in a fluidized bed, the carrier having a particle size of 200–1000 μm and a surface area of 20–1000 $m^2$/g,
   b) introducing an enzyme containing liquid medium by atomization into the fluidized bed, so as to fixate the enzyme on the carrier, and
   c) removing volatile components of the liquid medium from the carrier in the fluidized bed.

2. The process of claim 1, wherein the carrier comprises an inorganic material having a substantially hydrophilic surface, which is essentially insoluble in hydrophilic or hydrophobic liquids or mixtures thereof.

3. The process of claim 2, wherein the carrier is selected from the group consisting of silicas, zeolites, aluminas and kaolins.

4. The process of claim 1, wherein the carrier comprises an inorganic material selected from the group consisting of silicas, zeolites, aluminas and kaolins coated with organic moieties so as to provide a substantially hydrophobic surface.

5. The process of claim 1, wherein the carrier comprises an organic polymer resin.

6. The process of claim 5, wherein the resin is an adsorbent resin.

7. The process of claim 6 wherein the adsorbent resin is a polyacrylate, a polymethacrylate, polystyrene cross-linked with divinylbenzene, polyurethane or polypropylene.

8. The process of claim 5 wherein the resin is an ion exchange resin.

9. The process of claim 8, wherein the ion exchange resin is an anion exchange resin.

10. The process of claim 9, wherein the ion exchange resin is a weakly basic anion exchange resin.

11. The process of claim 1, wherein the carrier has an average pore size of 10–500 nm.

12. The process of claim 1, wherein the carrier has a particle size of 400–700 µm.

13. The process of claim 1, wherein said liquid medium is an aqueous medium.

14. The process of claim 1, wherein the enzyme is a lipase.

15. The process of claim 14, wherein the lipase is derived from a strain of the genus Humicola (also known as Thermomyces), Pseudomonas, Candida, or Rhizomucor.

16. The process of claim 15, wherein the lipase is derived from the species *H. lanuginosa* (also known as *Thermomyces lanuginosa*), *C. antarctica* or *R. miehei*.

17. A process for enzymatic modification of an organic compound comprising contacting in a reaction medium essentially devoid of free water said organic compound with an immobilized enzyme produced by the process of claim 1.

18. The process according to claim 17, wherein the enzyme immobilized is lipase, and the modification is a trans-esterification reaction comprising contacting a first reactant which is a fatty acid ester, and a second reactant which is another fatty acid ester, an alcohol or a free fatty acid with the immobilized lipase.

19. The process of claim 18, wherein the first reactant is a triglyceride.

20. The process of claim 18, wherein the second reactant is a fatty acid ester, and the lipase is positionally specific.

21. The process of claim 18, wherein the first and the second reactants are different triglycerides or different mixtures of triglycerides, and the lipase is positionally 1,3-specific.

22. The process of claim 18, wherein the reaction medium consists essentially of triglycerides.

23. The process of claim 18, wherein the reaction medium comprises an organic solvent.

24. A process for producing an immobilized enzyme preparation for use in an organic medium essentially devoid of free water, comprising:

a) contacting in a fluidized bed an enzyme containing liquid medium with a particulate porous carrier having a particle size of 200–1000 µm and a surface area of 20–1000 m$^2$/g, substantially hydrophobic surface, so as to adsorb the enzyme on the carrier, b) introducing a hygroscopic substance, so as to suppress agglomeration of the carrier by absorbing excess liquid, and c) removing volatile components of the liquid medium and the hygroscopic substance from the resulting product in the fluidized bed.

25. The process of claim 24, wherein the hygroscopic substance is particulate having a particle size which is smaller than the particle size of the carrier, and wherein the hygroscopic substance can be removed in step (c) by inserting at the top of the fluidized bed a filter having a pore size which will allow the hygroscopic substance to pass through.

26. The process of claim 25, wherein the hygroscopic substance is a silica material.

27. A process for producing an immobilized enzyme preparation for use in an organic medium essentially devoid of free water, comprising:

a) introducing into a fluidized bed an enzyme containing liquid medium by atomization onto a particulate porous carrier having a particle size of 200–1000 µm and a surface area of 20–1000 m$^2$/g and a substantially hydrophilic surface, so as to fixate the enzyme on the carrier, wherein the liquid is introduced in an amount such that substantially no agglomeration of the carrier occurs, and b) removing volatile components of the liquid medium from the resulting product in the fluidized bed.

* * * * *